(12) United States Patent
Inoue et al.

(10) Patent No.: US 8,168,436 B2
(45) Date of Patent: May 1, 2012

(54) METHOD FOR DETERMINING QUANTITY OF PEPTIDE COMPOUND HAVING PHENYLALANINE RESIDUE AT N-TERMINUS

(75) Inventors: Yoshihisa Inoue, Osaka (JP); Mikhail Rekharsky, Hyogo (JP); Kimoon Kim, Pohang (KR); Yong Ho Ko, Pohang (KR); Narayanan Selvapalam, Pohang (KR)

(73) Assignee: Japan Science and Technology Agency, Saitama (JP)

( * ) Notice: Subject to any disclaimer, the term of this patent is extended or adjusted under 35 U.S.C. 154(b) by 473 days.

(21) Appl. No.: 12/446,718

(22) PCT Filed: Oct. 23, 2007

(86) PCT No.: PCT/JP2007/070656
§ 371 (c)(1),
(2), (4) Date: Apr. 22, 2009

(87) PCT Pub. No.: WO2008/050769
PCT Pub. Date: May 2, 2008

(65) Prior Publication Data
US 2010/0238969 A1    Sep. 23, 2010

(30) Foreign Application Priority Data
Oct. 23, 2006   (JP) ................. 2006-288000

(51) Int. Cl.
*G01N 33/00* (2006.01)
(52) U.S. Cl. .................. 436/86; 436/147; 436/815
(58) Field of Classification Search .............. 436/86, 436/147, 815
See application file for complete search history.

(56) References Cited

U.S. PATENT DOCUMENTS

2004/0265237 A1   12/2004   Kim et al.
2005/0080068 A1   4/2005   Isaacs et al.

FOREIGN PATENT DOCUMENTS

| JP | 2005-503415 A | 2/2005 |
| WO | 03/024978 | 3/2003 |

OTHER PUBLICATIONS

U.S. Appl. No. 12/463,889 entitled "Method for Determination of Presence or Absence of Peptide Compound $PYY_{3-36}$," to Inoue et al., which application is a Continuation of PCT/JP2007/070785, filed Oct. 25, 2007.
U.S. Appl. No. 12/514,280 entitled "Method for Determination of Presence or Absence of Peptide Compound $PYY_{3-36}$," to Inoue et al., which application is the National Stage of PCT/JP2007/070785, filed Oct. 25, 2007.
M. Rekharsky, et al., Chiral Recognition in Cucurbituril Cavities, Journal of the American Chemical Society, Nov. 22, 2006, vol. 128, p. 14871-14880. Sures, I.; Crippa, M. Proc. Natl. Acad. Sci. 1984, 81, p. 380-384.
Bevins, C.L.; Zasloff, M. Annu. Rev. Biochem. 1990, 59, p. 395-414.
Carraway, R.E.; Mitra, S.P.; Muraki, K. Regul. Pept. 1990, 29, p. 229-239.
Carraway, R.E.; Cochrane, D.E.; Mitra, S.P. Regul. Pept. 1988, 22, p. 303-314.
Carraway, R.E.; Mitra, S.P. Peptides. 1990, 11, p. 747-752.

*Primary Examiner* — Jill Warden
*Assistant Examiner* — Monique Cole
(74) *Attorney, Agent, or Firm* — Greenblum & Bernstein, P.L.C.

(57) ABSTRACT

The present invention provides a method for quantifying a peptide compound having a phenylalanine residue at the N-terminal, comprising measuring the content of heat generated by mixing 1) a peptide compound having a phenylalanine residue at the N-terminal, 2) cucurbit[7]uril, and 3) a metal ion in a solution.

4 Claims, 3 Drawing Sheets

SEQUENCE LISTING

<160> NUMBER OF SEQ ID NOS: 3

<210> SEQ ID NO 1
<211> LENGTH: 9

```
<212> TYPE: PRT
<213> ORGANISM: Homo sapiens

<400> SEQUENCE: 1

Phe His Pro Lys Arg Pro Trp Ile Leu
1               5

<210> SEQ ID NO 2
<211> LENGTH: 7
<212> TYPE: PRT
<213> ORGANISM: Homo sapiens
<220> FEATURE:
<223> OTHER INFORMATION: This peptide is N-term conjugated to a pyruvic
      acid

<400> SEQUENCE: 2

Gly Lys Arg Pro Trp Ile Leu
1               5

<210> SEQ ID NO 3
<211> LENGTH: 8
<212> TYPE: PRT
<213> ORGANISM: Homo sapiens

<400> SEQUENCE: 3

His Pro Lys Arg Pro Trp Ile Leu
1               5
```

METHOD FOR DETERMINING QUANTITY OF PEPTIDE COMPOUND HAVING PHENYLALANINE RESIDUE AT N-TERMINUS

TECHNICAL FIELD

The present invention relates to a method for quantifying a peptide compound having a phenylalanine residue at the N-terminal.

BACKGROUND ART

Xenopsin-related peptides (Non-Patent Documents 1 and 2) can act as neurotransmitters, neuromodulators, and local hormones. In recent years, attention has particularly focused on their function as local hormones.

Xenopsin-related peptides acting as a local hormone are important in that they have gastric control functions (for example, a function that controls mammalian food intake), and are considered effective for treatment of obesity.

It is already known that such xenopsin-related peptides are present in a peptide mixture comprising xenopsin and a variety of xenopsin-related peptides having the same or similar amino acid sequences from the C-terminal and contained in extract from a mammalian stomach, etc. (for example, extract from the stomach, liver, and brain of mouse (Non-Patent Document 3); extract from avian tissue (Non-Patent Document 4); and extract from dogs (Non-Patent Document 5)).

Therefore, an easy and accurate quantification of a specific xenopsin-related peptide in a peptide mixture is very important.

Known methods include a method comprising purifying a peptide mixture using various chromatography methods, and examining the purified peptide mixture using an immunoassay. The immunoassay has high sensitivity for a peptide with a widely different amino acid sequence.

However, xenopsin and a variety of xenopsin-related peptides in the extract have the same or similar amino acid sequences from the C-terminal; therefore, it is difficult to distinguish a specific xenopsin-related peptide from other peptide compounds to accurately quantify the specific peptide in immunoassay.

Non-Patent Document 1:
Sures, I.; Crippa, M. Proc. Natl. Acad. Sci. 1984, 81, p 380
Non-Patent Document 2:
Bevins, C. L.; Zasloff, M. Annu. Rev. Biochem. 1990, 59, p 395
Non-Patent Document 3:
Carraway, R. E.; Mitra, S. P.; Muraki, K. Regul. Pept. 1990, 29, p 229-239
Non-Patent Document 4:
Carraway, R. E.; Cochrane, D. E.; Mitra, S. P. Regul. Pept. 1988, 22, p 303-314
Non-Patent Document 5:
Carraway, R. E.; Mitra, S. P. Peptides. 1990, 11, p 747-752

DISCLOSURE OF THE INVENTION

Problems to be Solved by the Invention

The main object of the present invention is to provide a method for easily and accurately quantifying a peptide compound having a phenylalanine residue at the N-terminal.

Means for Solving the Problems

The present inventors conducted extensive research in view of the problem of the foregoing prior art. As a result, they found that a specific quantification method can achieve the aforementioned object. The present invention has been accomplished based on this finding.

Namely, the present invention relates to a method for quantifying a peptide compound having a phenylalanine residue at the N-terminal, as described below.

1. A method for quantifying a peptide compound having a phenylalanine residue at the N-terminal, comprising measuring the content of heat generated by mixing
   1) a peptide compound having a phenylalanine residue at the N-terminal,
   2) cucurbit[7]uril, and
   3) a metal ion
   in a solution.
2. The quantification method according to Item 1, wherein the peptide compound having a phenylalanine residue at the N-terminal is quantified in a peptide mixture comprising the peptide compound having a phenylalanine residue at the N-terminal and a peptide compound other than the peptide compound having a phenylalanine residue at the N-terminal.
3. The quantification method according to Item 1 or 2, wherein the peptide compound having a phenylalanine residue at the N-terminal is Phe-His-Pro-Lys-Arg-Pro-Trp-Ile-Leu-OH (SEC) ID NO: 1).

The method for quantifying a peptide compound having a phenylalanine residue at the N-terminal of the present invention includes the step of measuring the amount of heat generated by mixing.

1) a peptide compound having a phenylalanine residue at the N-terminal,
2) cucurbit[7]uril, and
3) a metal ion
in a solution.

Peptide Compound Having a Phenylalanine Residue at the N-Terminal

The peptide compound (hereinafter sometimes referred to as "peptide compound A") having a phenylalanine residue at the N-terminal may be oligopeptide, polypeptide, etc. with a phenylalanine residue at the N-terminal, and is not particularly limited. Examples of peptide compound A include Phe-His-Pro-Lys-Arg-Pro-Trp-Ile-Leu-OH(XP-2) (SEQ ID NO: 1), insulin, human neuromedin U-25, pig neuromedin U-25, etc.

Cucurbit[7]uril

Cucurbit[7]uril (hereinafter sometimes referred to as "CB[7]") is a barrel-shaped molecule, which is shown in FIG. 1.

The addition of CB[7] causes a reaction between peptide compound A and CB[7] (forming a complex), generating heat.

Peptide compound A cannot be quantified with high accuracy when cucurbiturils (e.g., cucurbit[6]uril, cucurbit[8]uril) other than cucurbit[7]uril are used.

Metal Ion

The addition of a metal ion suitably advances the reaction (complex formation) of CB[7] and peptide compound A in a peptide mixture. More specifically, metal ion is bound to CB[7], which effectively reduces the reaction between CB[7] and peptide compounds other than peptide compound A, and advances the reaction (complex formation) of peptide compound A with CB[7].

Examples of metal ions include $Li^+$, $Na^+$, $K^+$, $Rb^+$, $Cs^+$ and like alkali metal ions; $Be^{2+}$, $Mg^{2+}$, $Ca^{2+}$, $Sr^{2+}$, $Ba^{2+}$ and like alkaline earth metal ions; etc.

Quantification

The quantification method of the present invention includes the step of measuring the amount of heat generated by mixing peptide compound A, cucurbit[7]uril, and a metal ion in a solution.

In the quantification method of the present invention, the amount of heat generated by reacting (forming a complex) peptide compound A in a peptide mixture that comprises peptide compound(s) other than peptide compound A, with cucurbit[7]uril is first measured, and then the quantity of peptide compound A in the peptide mixture is determined according to the obtained heat content.

In the quantification method of the present invention, peptide compound A may be present in a peptide mixture singly or in a combination of two or more. When peptide compound A is present in a combination of two or more, peptide compound A can be quantified as a mixture.

Examples of peptide compounds other than peptide compound A contained in a peptide mixture include Pyr-Gly-Lys-Arg-Pro-Trp-Ile-Leu-OH(XP) (SEQ ID NO: 2), His-Pro-Lys-Arg-Pro-Trp-Ile-Leu-OH(XP-1) (SEQ ID NO: 3), neurotensin, etc., and their relevant peptides.

That is, according to the quantification method of the invention, peptide compound A contained in a peptide mixture that comprises peptide compounds having the same or similar amino acid sequences from the C-terminal can be accurately quantified.

The present quantification method focuses on the N-terminal of a peptide compound, rather than, as in the conventional method, the C-terminal of a peptide compound.

In the quantification method of the present invention, the concentration of a peptide mixture in a solution is not particularly limited, but is preferably 0.01 to 1 mmol/l, more preferably 0.03 to 0.5 mmol/l, and most preferably 0.05 to 0.1 mmol.

In the quantification method of the present invention, there is no limitation on the mole percentage of peptide compound A in a peptide mixture to be dissolved in a solution. In particular, according to the present method, peptide compound A can be accurately quantified even when the mole percentage of peptide compound A in a peptide mixture is about 1%.

The concentration of CB[7] in a solution is not particularly limited, but is preferably 0.1 to 10 mmol/l, more preferably 0.3 to 5.0 mmol/l, and most preferably 0.5 to 1.0 mmol/l.

Metal ion can be prepared by, for example, dissolving salt of the aforementioned metal ion in a solution.

Salts are not particularly limited. Preferable examples include natural salts that are dissolved in a solution, slightly acidic salts, and slightly basic salts that are dissolved in a solution.

Examples of neutral salts include $Na_2SO_4$, $K_2SO_4$, $MgSO_4$, NaCl, KCl, $MgCl_2$, $NaNO_3$, $KNO_3$, $Mg(NO_3)_2$, $Ca(NO_3)_2$, $Na_3PO_4$, $K_3PO_4$, etc.

Examples of slightly acidic salts include $NaH_2PO_4$, $KH_2PO_4$, etc.

Examples of slightly basic salts include $Na_2CO_3$, $NaHCO_3$, $K_2CO_3$, $KHCO_3$, $Na_2HPO_4$, $K_2HPO_4$, $CH_3COONa$, $CH_3COOK$, etc. Such salts can be used singly or in a combination of two or more. The concentration of salt in a solution is suitably determined according to the solubility, etc., of salt to be used, but is preferably 0.01 to 1 mol/l, more preferably 0.05 to 0.5 mmol/l, and most preferably 0.05 to 0.1 mmol/l.

Examples of solvents used for mixing the peptide mixture, CB[7], and metal ion are not particularly limited; examples include water, ethanol, acetic acid, acetonitrile, acetone, etc. Such solvents can be used singly or in a combination of two or more. In the present invention, water is preferably used as a solvent.

In particular, in the quantification method of the present invention, it is preferable to use water as a solvent and NaCl as a salt, the concentration of the NaCl being about 0.9% (i.e., normal saline solution).

The pH of the solution obtained by mixing the peptide mixture, CB[7], and metal ion is not limited, but is preferably 1 to 8, more preferably 3 to 7, and most preferably 6 to 7. In particular, peptide compound degradation can be effectively prevented at a pH of 3 or more.

The known calorimeters may be used for measurement of heat that is generated by mixing peptide compound A, cucurbit[7]uril, and metal ion in a solution. In the present invention, it is particularly preferable to use an isothermal titration calorimeter for measurement of heat.

The present quantification method will be described in detail below, showing the use of an isothermal titration calorimeter in a typical example.

Formation of Calibration Curve

Prior to the quantification of peptide compound A in a peptide mixture, heat generated by the addition of pure peptide compound A is measured.

The isothermal titration calorimeter may be used according to the conventional manner. Specifically, a peptide compound A-containing solution and a CB[7]-containing solution are first prepared, and a specified amount (e.g., 0.01 ml per each) of CB[7]-containing solution may be added dropwise to the peptide compound A-containing solution under thermal equilibrium.

The calibration curve can be prepared by plotting the molar ratio of peptide compound A and the added CB[7] on the abscissa, and the amount of heat generated at each addition on the ordinate.

The heat content generated by the addition of pure peptide compound A can be obtained by summing up the amounts of heat on the calibration curve.

In the preparation of a peptide compound A-containing solution and a CB[7]-containing solution, the aforementioned salts may be dissolved in the peptide compound A-containing solution and/or CB[7]-containing solution. Thereby, by adding the solution dropwise as mentioned above, 1) peptide compound A, 2) CB[7], and 3) metal ion can be mixed.

The peptide compound A-containing solution can be prepared by dissolving peptide compound A in the solvent.

The concentration of peptide compound A in the peptide compound A-containing solution is not particularly limited, but is preferably 0.01 to 1 mmol/l, more preferable 0.03 to 0.5 mmol/l, and most preferably 0.05 to 0.1 mmol/l.

When the peptide compound A-containing solution is dissolved in salt, the concentration of salt may be determined according to the solubility etc. of salt to be used; however, it is preferably 0.01 to 1 mmol/l, more preferably 0.05 to 0.5 mmol/l, and most preferably 0.05 to 0.1 mmol/l.

The CB[7]-containing solution may be prepared by dissolving CB[7] in the solvent.

The concentration of CB[7] in the CB[7]-containing solution is not particularly limited, but is preferably 0.1 to 10 mmol/l, more preferably 0.5 to 5 mmol/l, and most preferably 0.5 to 1 mmol/l.

It is preferable to dissolve salt in the CB[7]-containing solution. CB[7] can be suitably dissolved by salt dissolution.

The concentration of salt in the CB[7]-containing solution may be suitably determined in accordance with the solubility, etc. of salt to be used, but is preferably 0.01 to 1 mmol/l, more preferably 0.05 to 0.5 mmol/l, and most preferably 0.05 to 0.1 mmol/l.

Quantification of Peptide Compound A in a Peptide Mixture

Peptide compound A in a peptide mixture is quantified. Specifically, the quantification may be conducted following the same method described in the "Formation of Calibration Curve" above, except that a peptide mixture-containing solution obtained by dissolving a peptide mixture in a solvent is used in place of the peptide compound A-containing solution.

The concentration of the peptide mixture in the peptide mixture-containing solution may be almost the same as the concentration of the peptide compound A-containing solution described in the "Formation of Calibration", but is preferably 0.01 to 1 mmol/l, more preferably 0.03 to 0.5 mmol/l, and most preferably 0.05 to 0.1 mmol/l.

The mole percentage of peptide compound A in a peptide mixture can be calculated by dividing the total amount of heat generated each time the CB[7]-containing solution is added dropwise by the total amount of heat on the calibration curve.

Peptide compound A can be quantified using the above method.

Effect of the Invention

According to the quantification method of the present invention, a peptide compound having a phenylalanine residue at the N-terminal can be easily and accurately (range of error within approximately 1 to 2%) quantified. Specifically, in the present method, the peptide compound is quantified based on the amount of heat generated by a reaction (complex formation) of a peptide compound having a phenylalanine residue at the N-terminal with cucurbit[7]uril.

The present method provides an accurate quantification of a peptide compound with a phenylalanine residue at the N-terminal that is contained in a peptide mixture comprising peptide compound(s) in addition to a peptide compound with a phenylalanine residue at the N-terminal.

For example, the present method provides an accurate quantification of XP-2 that is contained in a peptide mixture comprising Pyr-Gly-Lys-Arg-Pro-Trp-Ile-Leu-OH(XP) (SEQ ID NO: 2), His-Pro-Lys-Arg-Pro-Trp-Ile-Leu-OH(XP-1) (SEQ ID NO: 3), Phe-His-Pro-Lys-Arg-Pro-Trp-Ile-Leu-OH(XP-2) (SEQ ID NO: 1), neurotensin, their relevant peptides, etc., those having the same or similar amino acid sequences from the C-terminal. XP-2 is a peptide compound secreted by the gastric mucosa when human and other animals feel full. XP-2 is an important compound in that it has gastric control functions (for example, a function that controls mammalian food intake), and is considered effective for treatment of obesity, etc.

The present method can provide an accurate xquantification even when a peptide compound having a phenylalanine reside at the N-terminal is contained in a peptide mixture in small amounts (for example, when the mole percentage of the peptide compound with a phenylalanine residue at the N-terminal in the peptide mixture is about 1%).

According to the quantification method of the present invention, the quality of pharmaceutical formulations containing xenopsin-related peptides (e.g., XP-2) can be suitably controlled.

BEST MODE FOR CARRYING OUT THE INVENTION

The present invention is described in further detail with reference to the following Example. However, the present invention is not limited thereto.

Example 1

Formation of Calibration Curve 0.1 mg of XP-2 was dissolved in a 0.1 mol/l NaCl solution (1.5 ml) to prepare a 0.056 mmol/l XP-2-containing solution.

CB[7] was dissolved in a 0.1 mol/l NaCl solution to prepare a 0.5 mmol/l CB[7]-containing solution.

The XP-2-containing solution (1.5 ml) was loaded into a reaction cell of an ultra-sensitive isothermal titration calorimeter VP-ITC (produced by MicroCal, Inc.). The colorimeter syringe was filled with the CB[7]-containing solution (0.25 ml).

Figure 1:
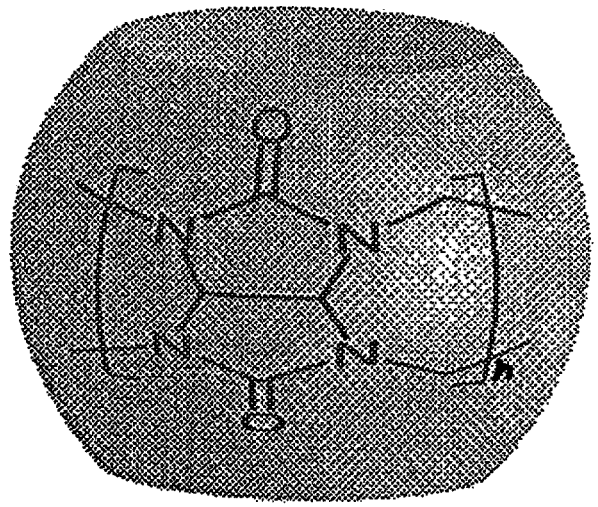
FIG. 1 shows a chemical structure of cucurbit[7]uril.
Figure 2:
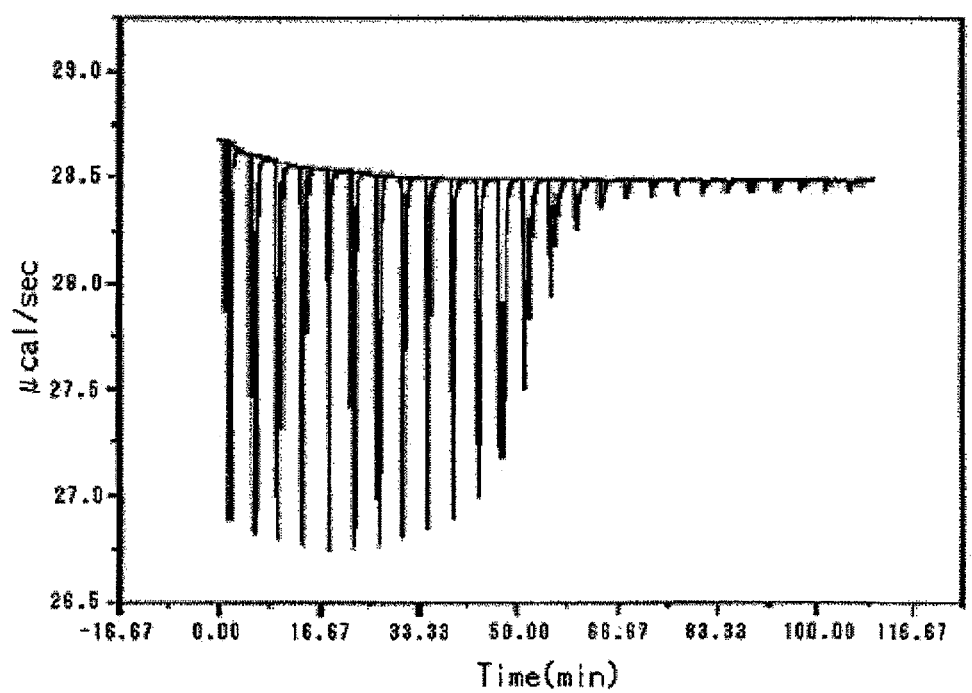
FIG. 2 is a graph showing the data of the heat content obtained in the "Formation of Calibration Curve" in Example 1.

The calorimeter was set in the state of thermal equilibrium, and 0.01 ml (per each) of CB[7]-containing solution was added to a reaction cell a total of 25 times. The generated heat data is shown in FIG. 2.

Figure 3:
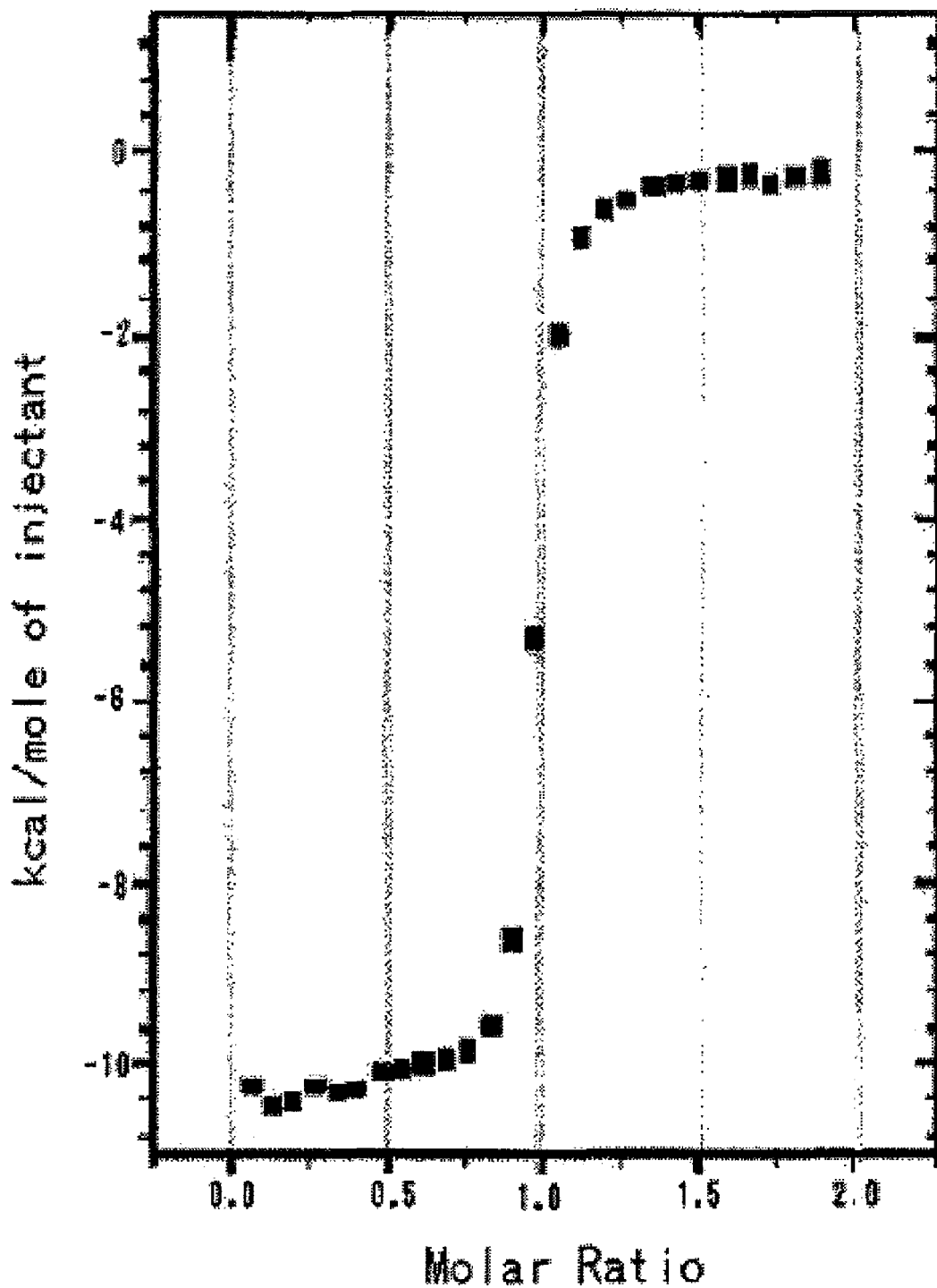
FIG. 3 is a graph in which the heat content obtained by automatically integrating the data of FIG. 2 is plotted.

The resulting data was automatically integrated using ORIGIN 7.0 (produced by MicroCal Inc.) The results are shown in FIG. 3. The total value of heat obtained according to the sum of each plotted point is 135. The results reveal that when the concentration of XP-2 in a 0.1 mol/l NaCl solution is 0.056 mmol/l, 135 kcal of heat is generated.

Quantification of XP-2 in Peptide Mixture

Subsequently, a xenopsin mixture (peptide mixture) in which the mole percentage of XP-2 is 4% was dissolved in a 0.1 mol/l NaCl solution to prepare a 0.056 mmol/l mixture solution. The prepared mixture solution was loaded into a reaction cell of the calorimeter. The colorimeter syringe was filled with 0.25 ml of CB[7]-containing solution.

Figure 4:
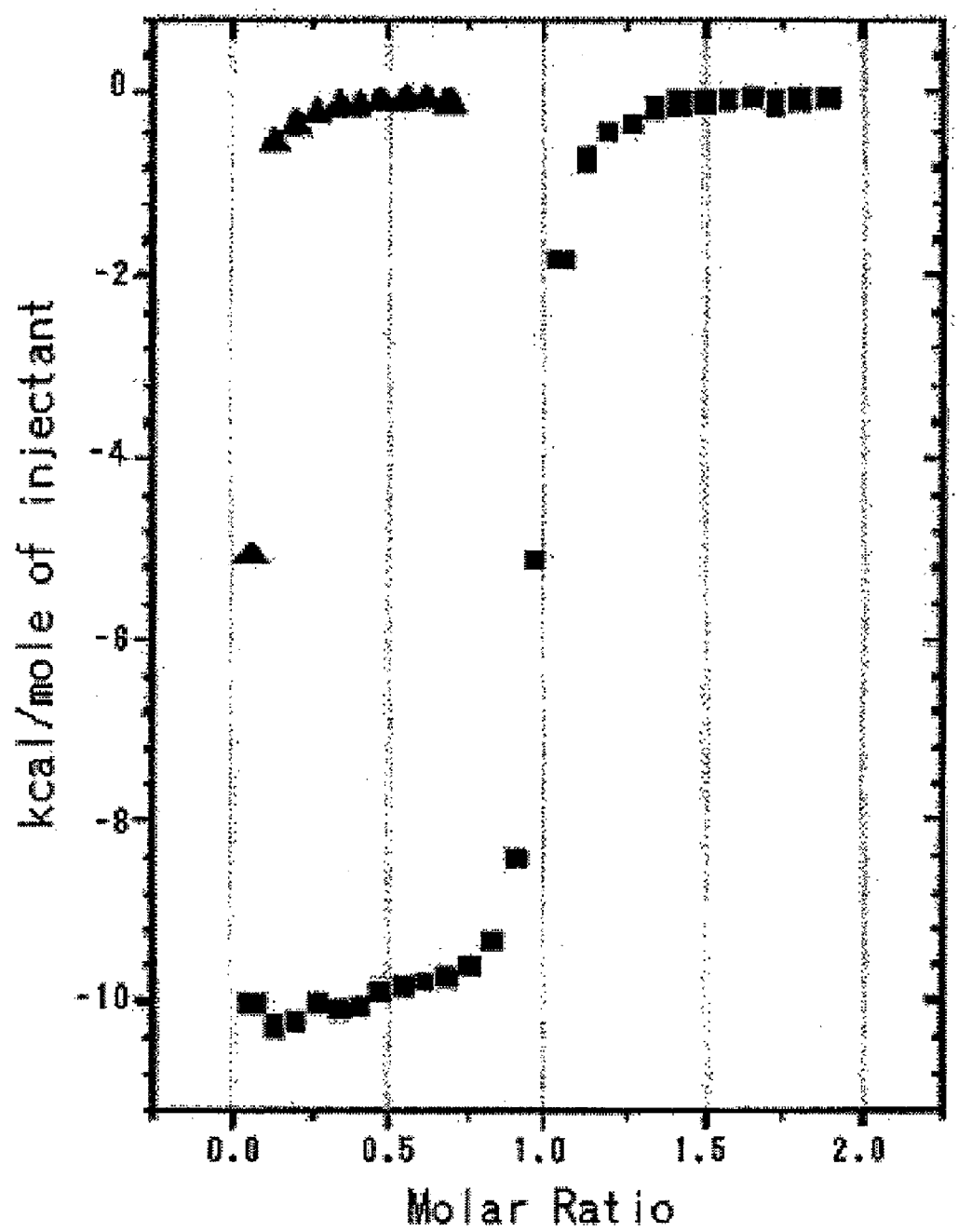
FIG. 4 is a graph showing the plot of FIG. 3 as well as the amount of heat obtained by automatically integrating the data of heat generated in the "Quantification of XP-2 in Peptide Mixture" in Example 1.

The heat was measured using the same method described above, and the resulting data was automatically integrated. The results are shown in the left side of FIG. 4. The total amount of heat obtained according to the sum of each plotted point is 6 kcal. The plot of FIG. 3 is also shown in the right side of FIG. 4 for comparison.

6/135=0.044; accordingly, it is confirmed that the mole percentage of XP-2 in the xenopsin mixture is 4.4%.

The results indicate that the present quantification method achieves a high accuracy quantification of XP-2.

The invention claimed is:

1. A method for quantifying a peptide compound having a phenylalanine residue as the N-terminal residue, said method comprising measuring the amount of heat generated by mixing
   1) the peptide compound having a phenylalanine residue as the N-terminal residue,
   2) cucurbit[7]uril, and
   3) a metal ion
in a solution,
wherein the amount of heat generated by the solution is compared to a calibration curve to determine the quantity of the peptide compound in the solution.

2. The quantification method according to claim 1, wherein the peptide compound having a phenylalanine residue at the N-terminal is quantified in a peptide mixture comprising the peptide compound having a phenylalanine residue at the N-terminal and a peptide compound other than the peptide compound having a phenylalanine residue at the N-terminal.

3. The quantification method according to claim 1, wherein the peptide compound having a phenylalanine residue at the N-terminal is Phe-His-Pro-Lys-Arg-Pro-Trp-Ile-Leu-OH.

4. The quantification method according to claim 2, wherein the peptide compound having a phenylalanine residue at the N-terminal is Phe-His-Pro-Lys-Arg-Pro-Trp-Ile-Leu-OH.

* * * * *